United States Patent [19]

Pitha

[11] Patent Number: 4,546,097

[45] Date of Patent: Oct. 8, 1985

[54] SAPONIN-BASED POLYETHER POLYOLS, PHARMACEUTICAL COMPOSITIONS AND A METHOD OF USING SAME

[75] Inventor: Josef Pitha, Baltimore, Md.

[73] Assignee: The United States of America as represented by the Department of Health and Human Services, Washington, D.C.

[21] Appl. No.: 548,849

[22] Filed: Nov. 4, 1983

[51] Int. Cl.⁴ .................... A61K 31/705; C07J 17/00
[52] U.S. Cl. ........................................ 514/26; 536/5; 536/6; 536/6.1
[58] Field of Search ............... 424/182; 536/5, 6, 6.1, 536/6.2, 6.3; 514/26

[56] References Cited

U.S. PATENT DOCUMENTS

| | | | |
|---|---|---|---|
| 2,479,761 | 8/1949 | Miescher et al. | 536/5 |
| 3,314,936 | 4/1967 | Ames et al. | 260/209 |
| 3,317,508 | 5/1967 | Winquist et al. | 260/209 |
| 3,324,108 | 6/1967 | Moller et al. | 260/209 |
| 3,538,078 | 11/1970 | Kaiser et al. | 536/6.1 |
| 3,712,884 | 1/1973 | Voigtlander et al. | 536/6.1 |
| 3,753,974 | 8/1973 | Kaiser et al. | 536/6.1 |
| 3,865,806 | 2/1975 | Knodel | 260/209 |
| 4,011,389 | 3/1977 | Langdon | 536/4 |
| 4,230,824 | 10/1980 | Nodelman | 521/167 |
| 4,242,502 | 12/1980 | Malinow et al. | 536/5 |
| 4,332,936 | 6/1982 | Nodelman | 536/120 |

OTHER PUBLICATIONS

"The Merck Index", 9th Ed., 1976, 3137, p. 417.

*Primary Examiner*—Johnnie R. Brown
*Attorney, Agent, or Firm*—Holman & Stern

[57] ABSTRACT

Digitonin and digitonin-related saponins are derivatized by alkoxylation. The adducts have lower toxicity, higher solubility, and reduced ability to form insoluble complexes with cholesterol, as compared to the starting material. The adducts are particularly useful as solubilizing agents for lipophilic drugs and as mycoplasma suppressors in cell cultures.

21 Claims, 3 Drawing Figures

SAPONIN-BASED POLYETHER POLYOLS, PHARMACEUTICAL COMPOSITIONS AND A METHOD OF USING SAME

BACKGROUND OF THE INVENTION

Digitonin, a saponin having well-recognized pharmacological properties, is commonly obtained by extraction from plants of the genus Digitalis, particularly from seeds of *Digitalis purpurea*. The primary extract is typically purified by precipitation with cholesterol to yield a mixture of digitonin and digitonin-related saponins. Owing to the difficulty of separating digitonin from this mixture, the purified extract is generally employed in pharmaceutical applications, rather than purified digitonin.

While effective, these purified saponin extracts have several disadvantages as a pharmaceutical. The low solubility of the saponins in aqueous solution makes them difficult to administer. The compounds are fairly toxic, typically producing acute inflammation in parenteral administration and exhibiting strong hemolytic effects. The reported $LD_{50}$ of digitonin in rats by i.v. administration is 4 mg/kg. The digitonin property of forming insoluble complexes with cholesterol has been employed pharmaceutically to regulate cholesterol adsorption in humans, as exemplified by U.S. Pat. No. 4,242,502 to Malinow, et al. However, this same property has been implicated in the toxic side effects experienced in parenteral administration of digitonin and digitonin-related saponins.

SUMMARY OF THE INVENTION

The invention provides a method for solubilizing digitonin and digitonin-related saponins comprising alkoxylating the saponin starting material with conventional alkoxylation agents such as alkylene oxides or diglycidyl ethers. The product saponin-based polyether polyols have low toxicity, high solubility, and a decreased capacity for forming insoluble complexes with cholesterol. The adducts of the present invention further have particular application for solubilization of lipophilic pharmaceuticals and suppression of mycoplasmas in cell cultures.

DETAILED DESCRIPTION OF THE INVENTION

Figure 1:
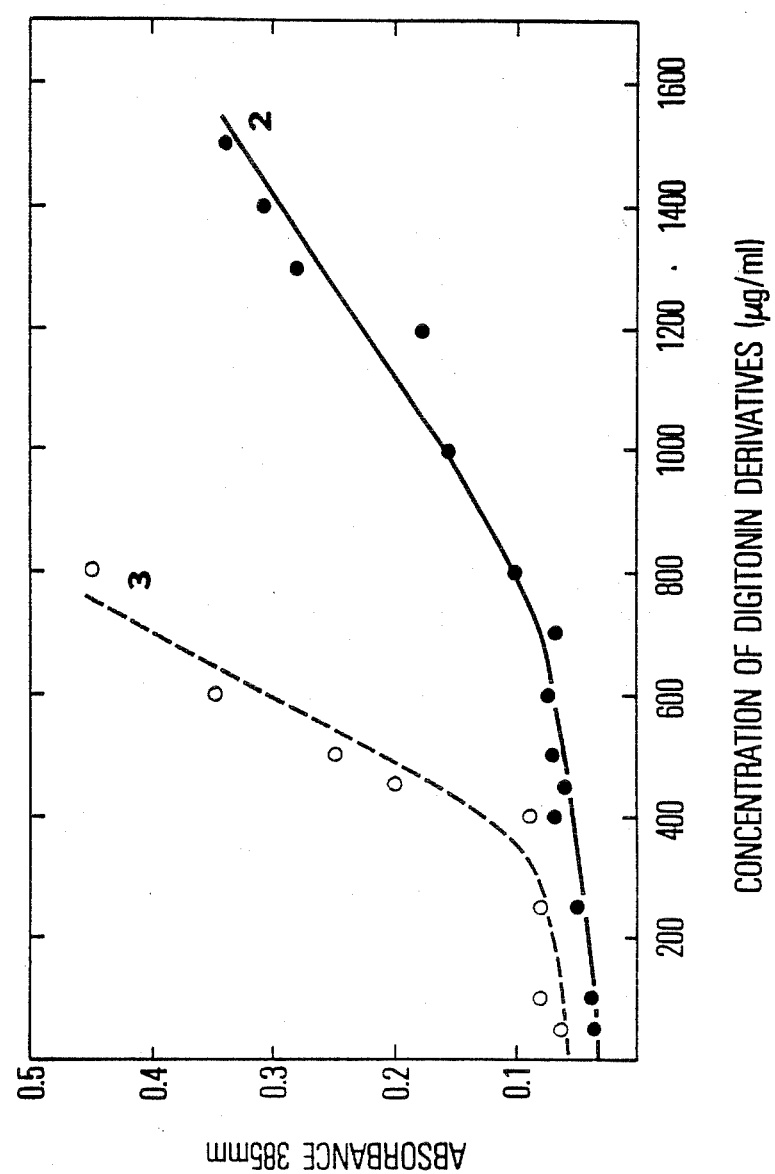
FIG. 1 is a graphic illustration of the dependence of absorbence at 385 nm of aqueous solution of iodine on the concentration of digitonin derivatives according to the invention.

Digitonin and digitonin-related saponins are alkoxylated in a conventional alkoxylation process to provide the saponin-based polyether polyols of the invention. Saponins comprising either purified digitonin, purified digitonin-related saponins, or a mixture of digitonin and digitonin-related saponins may be employed as starting material. Useful saponin starting materials broadly include plant extracts containing digitonin and digitonin-related saponins, preferably purified with respect to digitonin by conventional purification procedures such as precipitation or recrystallization. Extracts of plant material derived from plants of the genus Digitalis are preferred, owing to their high digitonin content. For the purposes of the present disclosure, the term "digitonin-related saponins" is defined as saponins which precipitate with digitonin on treatment with cholesterol under the classic precipitation procedures described by Gisvold in *J. Am. Pharm. Assoc.* 23:664 (1934). Arbitrarily assigning digitonin a precipitation coefficient with cholesterol of 100, the term "digitonin-related saponins" may then also be defined as those saponins which have a precipitation coefficient of at least about 100 with cholesterol; that is, if under the Gisvold process conditions digitonin forms a precipitate with cholesterol in a relative amount of 100, the digitonin-related saponins will form a precipitate with cholesterol in an amount of at least about 100, reflecting an at least about equivalent capacity to form insoluble complexes with cholesterol. The term "digitonin-related saponins" specifically includes digalonin, gitonin, and desglucodigitonin. An exemplary starting material is a commercial digitonin preparation of the type previously mentioned, comprising an extract of saponins from the seeds of *Digitalis purpurea*, further purified by treatment with cholesterol to precipitate digitonin and digitonin-related saponins. The amount of digitonin and the specific digitonin-related saponins present in the cholesterol-purified extracts will vary, depending upon, for example, the composition of the plant extract, and the exact extraction/precipitation conditions employed. However, such purified extracts typically contain from about 40% to 80% digitonin and include such digitonin-related saponins as digalonin, desglucodigitonin, gitonin, tigonin, and dig d', as described, for example, in Tschesche, et al., *Tetrahedron* 19:621, 1963. Useful preparations of digitonin for the starting material of the present invention include the typical preparations set forth in the *Merck Index*, 9th Ed., 3137 (1976).

The saponin-based polyether polyols of the invention are prepared from the saponin starting material in a conventional alkoxylation process, particularly alkoxylation processes generally useful in the preparation of ethers from organic polyhydroxy compounds, especially glycosides. Broadly, the saponin-based polyether polyols of the invention are prepared by reacting known alkoxylation reagents such as alkylene oxides and diglycidyl ethers with the saponin starting material under conditions which result in the addition of oxyalkylene groups to the free hydroxyl groups of the saponins employed. As is well-known in the art, the resulting adducts may vary considerably in their chemical structure, particularly with respect to the degree of substitution of each molecule and the number of oxyalkylene groups added to each free hydroxyl group, depending upon the various process parameters. Polyether polyols within the scope of the invention comprise saponin-based polyether polyols obtained by alkoxylation of the specified saponin starting materials, further characterized by low toxicity on parenteral administration, high solubility, and a low capacity for forming insoluble complexes with cholesterol. Saponin-based polyether polyols having an $LD_{50}$ (i.v. in mice)$\leq 50$ mg/kg, a solubility in water at 20° C. of at least about 100 g./l., and a precipitation coefficient with cholesterol of less than about 25, obtained by alkoxylation of digitonin, digitonin-related saponins, or mixtures thereof are preferred, especially saponin-based polyether polyol compositions so characterized obtained by alkoxylation of digitonin mixtures comprising purified plant extracts. Typically, such saponin-based polyethers are obtainable by alkoxylation with sufficient amounts of alkylene oxide or diglycidyl ether to obtain an average substitution of about 0.5 to 2 oxyalkylene groups per molecule of saponin. It is believed the oxyalkylene groups preferentially add to unsubstituted primary hydroxyl groups of the saponin molecule in the course of the reaction to form theoretical structures as exemplified infra.

Suitable exemplary processes for obtaining the polyether polyols of the invention are the alkoxylation processes described in the following patents: U.S. Pat. Nos. 4,230,824; 3,865,806; 4,332,936; 3,324,108; 3,317,508; and 3,314,936, with the caveat that the product saponin-based polyethers have the requisite low toxicity, high solubility, and low capacity for complexing with cholesterol, and retain biological properties consistent with their intended use. Alkoxylating agents comprising $C_2$–$C_6$-alkylene oxides and their simple derivatives, and diglycidyl ethers prepared from $C_2$–$C_6$-alkane diols are particularly suggested, especially ethylene oxide, 1,2 propylene or butylene oxide and epichlorohydrin.

Generally, the reaction should be carried out in an inert, non-toxic solvent such as water, employing alkaline catalysts such as alkali metal hydroxides.

EXAMPLES

Example I

Synthesis of Digitonin Derivative 2.

Digitonin (Sigma Chemical Co. St. Louis, MO) (1 g, 0.8 mmol) was suspended in a solution of sodium hydroxide (200 mg) in water (6.5 ml), and propylene oxide (1 ml, 15 mmol) was added. The mixture was then stirred at 60° C. for 1 hr. and at room temperature overnight. The clear solution was then neutralized by hydrochloric acid and dialyzed for one day against distilled water. Dialysis tubing from regenerated cellulose (A. H. Thomas Co., Philadelphia, PA) was used with a nominal molecular weight cutoff of 8000–12000. Freeze drying of the contents of dialysis tubing yielded derivative 2 as a solid foam-like material (1 g.). Solubility of Derivative 2 in water was about 21 g/100 ml at room temperature. This compound tended to occlude solvents and thus, elemental analysis could not be used to estimate its degree of substitution. Field desorption mass spectrometry (NIHLB assembly, Bethesda, MD) was used for that purpose; analysis of the relative intensities of peaks (mass of digitonin derivative plus sodium ion) gave the following distribution at the molecular weight: unsubstituted (36%), monosubstituted (36%), disubstituted (19%) trisubstituted (6%), tetrasubstituted (2%), and pentasubstituted (1%); thus, the average degree of substitution is about 1.4.

Example II

Synthesis of Digitonin Derivative 3.

The same procedure as in Example I was followed, except using 1,4 butanediol diglycidyl ether (Aldrich Chemical, Philadelphia, PA) in place of propylene oxide, and 8 g. digitonin. The yield was 6.9 g of derivative 3. The solubility of derivative 3 in water at room temperature was 11 g/100 ml. To estimate the degree of substitution in derivative 3, the compound was exhaustively methylated and thereafter analyzed for content of carbon and methoxyl groups. For that purpose, derivative 3 (1 g, about 1 mmol) was dissolved in dimethylformamide (10 ml) and sodium hydride (0.4 g) was gradually added to the solution. The reaction was allowed to proceed for 30 min with stirring at room temperature. The viscous mixture was then cooled to 0° C. and methyl iodide (4.5 g) was added dropwise and stirring was continued for another 12 hrs. The reaction was terminated by addition of methanol; then the reaction mixture was dialyzed against water and freeze dried. Product 4 was a white powder (0.92 g) which was very hygroscopic; completion of methylation was established by absence of absorption in the region of hydroxyl stretching vibration (3100–3600 cm$^{-1}$) in the infrared spectrum (Beckman Infrared Spectrophotometer 1R12). Compound 4 was repeatedly dissolved in water and evaporated to dryness in vacuo to eliminate all traces of organic solvents and was then analyzed for carbon content and for content of methoxy groups (Zeissel method). In two separate preparations of 4 these values were found to be 33.1% and 35.8% for methoxyl and 50.0% and 56.3% for carbon, respectively. From the ratio of methoxyl to carbon contents the average degree of substitution was calculated and found to be close to 1.

Control experiments in which only digitonin or only 1,4-butanediol diglycidyl ether were treated with aqueous alkali as above, were performed with the following results. From self-condensation of digitonin less than 1% of the water soluble material could be isolated. If the products of self-condensation of digitonin were dissolved in 50% aqueous dimethyl-formamide, less than 1% was nondialyzable. The products of self-condensation of 1,4-butanediol diglycidyl ether were water soluble but more than 97% was dialyzable.

Exemplary theoretical average structures for derivatives 2 and 3 are given:

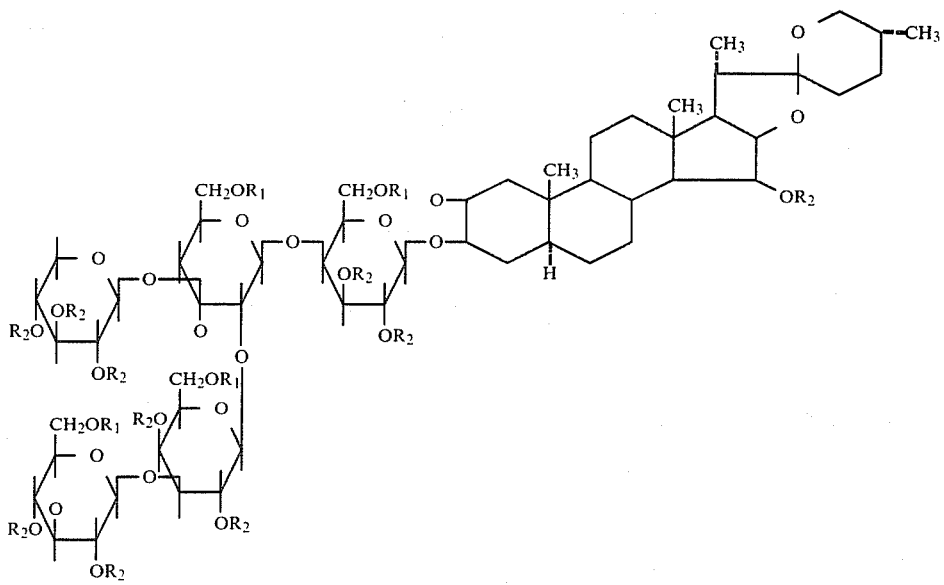

Digitonin (1): R=H; $R_2$=H
Derivative (2): $R_1$=CH$_2$CHOHCH$_3$OrH; $R_2$=H
Derivative (3): $R_1$=CH$_2$CHOHCH$_2$(OC$_4$H$_8$O)CH$_2$CHOHCH$_2$OH or H; $R_2$=CH$_3$ Since the commercial digitonin used in the condensation contains several other saponins these were derivatized along with digitonin and were present in the products. Derivatives 2 and 3 were not contaminated by products of self-condensation reactions of either digitonin or epoxides. Derivatives 2 and 3, in spite of being obviously mixtures, had uniform solubility properties. Digitonin dissolves in water only slightly, whereas derivatives 2 and 3 dissolve clearly both in water and chloroform.

Example III

Measurement of micellar space in aqueous solutions of 2 and 3.

The method (described *J. Phys. Chem.* 63:1671 1959 and *Eur. J. Biochem.* 94:11, 1979) is based on the color change of iodine that takes place when micelles are formed in the aqueous solution of iodine (30 mg/l). The absorbancy (Cary 14M recording UV spectrophotometer) at 385 nm, which is proportional to the micellar space, was measured as the function of concentration of derivatives 2 and 3 in solution. Results are illustrated in FIG. 1. Self-association of derivatives 2 and 3 was apparent from the concentration dependence of nonpolar (i.e., micellar) space in aqueous solutions of derivatives 2 and 3. This space is relatively small when only non-associated species of amphiphile are present in solution but becomes prominent when the higher order self-associated species, micelles, start to be formed; this occurred at concentrations of 700 μg/ml for 2 and 300 μg/ml for 3.

Example IV

Molecular weight determination by vapor pressure osmometry.

Chloroform, which was used as a solvent, was purified by washing with solutions of sulfuric acid, sodium hydroxide, and with water; then chloroform was dried and redistilled. For measurements the vapor pressure osmometer (Hitachi model 117) was used; the osmometer was calibrated using pentaerythrityl tetrastearate (molecular weight 1202) and polystyrene standard ($\overline{M}_w$: $\overline{M}_n$=1.04; $\overline{M}_w$=9000). All measurements were performed at 29.9° C.

Figure 2:
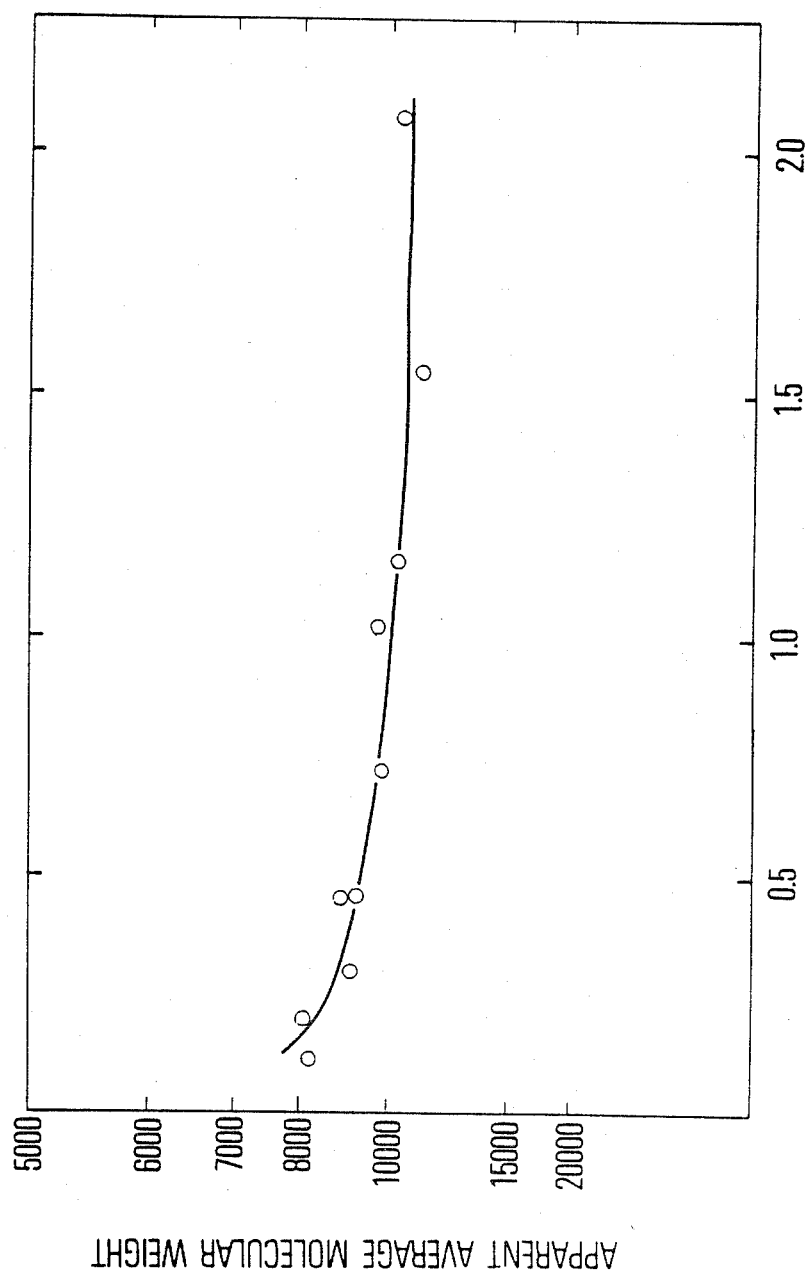
FIG. 2 is a graphic illustration of the concentration dependence of the apparent average molecular weight of a digitonin derivative according to the invention as measured in chloroform by vapor pressure osmometry.

Derivative 3 was found to be strongly self-associated in chloroform solutions. Results of the concentration dependence of apparent molecular weight, as measured by vapor pressure osmometry, are in FIG. 2. Even at concentration 0.1% the measured molecular weight of derivative 3 is five to six times higher than the MW calculated for the monosubstituted product.

Example V

Precipitation of digitonin and its derivatives by cholesterol.

To a solution of a saponin (digitonin on derivatives 2 and 3 from Examples I and II) (10 mg) in absolute ethanol (1 ml) was added a solution of cholesterol (40 mg) in ethanol (95%, 6.0 ml). Each mixture was heated at 60° C. for 10 min and then allowed to stand for 1 hr before the precipitate was collected, dried, and weighed. Amounts of precipitate were 41 mg, 6 mg, and 0 mg for digitonin and derivatives 2 and 3, respectively.

Digitonin forms insoluble complexes with cholesterol. The substitution of digitonin by epoxides supresses this complexation. Under the experimental conditions, when digitonin formed a precipitate with cholesterol in a relative amount of 100, derivatives 2 and 3 formed a precipitate in relative amounts of only 15 and 0, respectively.

Example VI

Binding of cholesterol-digitonin derivatives by equilibrium dialysis.

Dialysis tubing (Example I) was washed extensively with boiling water and with ethanol. Dialysis was performed in ethanol (95%). The solution of digitonin derivative (volume: 1 ml) was placed inside of the dialysis tubing and a solution of [$^{14}$C]-cholesterol (NE Nuclear, Boston, Mass.) placed outside (volume: 2 ml). After equilibration for six days the concentration of radioactivity inside and outside of the dialysis bag was measured by liquid scintillation counting (Beckman LS-250 Scintillation System).

Derivatives 2 and 3 did not permeate through the dialysis membrane; consequently, equilibrium dialysis could be used to study the interaction of cholesterol with these derivatives which may occur in ethanol solutions and in which soluble complexes may be formed. In equilibrium dialysis with derivative 3 the equilibrium concentrations of cholesterol found inside the dialysis tubing, which contained increasing amounts of derivative 3, were within experimental error and equal to those found in solutions outside the tubing, where there was no digitonin derivative present (Table I). Consequently, no complex formation was detected by this method.

Equilibrium dialysis in cholesterol-derivative 3 system.

TABLE I

| Concentration of derivative 3 inside dialysis tubing | Distribution of [$^{14}$C]-Cholesterol | |
|---|---|---|
| | cpm/ml inside of dialysis tubing (corrected for background cpm) | cpm/ml outside of dialysis tubing (corrected for background cpm) |
| 0 mg/ml | 13,820 | 13,940 |
| 2 mg/ml | 13,980 | 14,020 |
| 10 mg/ml | 14,380 | 14,920 |
| 50 mg/ml | 14,940 | 14,680 |

Example VII

Solubilizing effects of digitonin derivatives.

Lipophilic compound, in excess, was introduced into stoppered polyethylene test tube (volume 1.2 ml), containing phosphate buffered isotonic saline (1 ml) without or with derivative 2 or 3 (50 mg). After equilibration by rotation overnight at 20°–22° C. the suspension was centrifuged and the clear supernatant was used to measure spectrophotometrically (Ex. II) the concentration of the solubilized lipophilic compound.

The solubility of drugs and related compounds is of considerable theoretical and practical importance in pharmaceutical science, and development of effective solubilizing agents present a useful complement to the development of new drugs. Derivatives 2 and 3 are very potent solubilizers of lipophilic compounds. Results of solubilization experiments are given in Table II; the solubility of some of the compounds in water was increased by two to three orders of magnitude even at moderate solubilizer concentrations. Derivative 3 seems to be a more potent solubilizer of vitamin A than any cyclodextrin or polymethionine sulfoxide previously tested.

TABLE II

Solubilization of nonpolar compounds by derivatives of digitonin in phosphate buffered isotonic saline

| Solubilized compound | | Solubilizing agent | |
|---|---|---|---|
| | none | Derivative 2 (5% solution) | Derivative 3 (5% solution) |
| β-Ionene | 7.3 μg/ml | 2050 μg/ml | 1820 μg/ml |
| Retinol | <4 μg/ml | 1600 μg/ml | 2500 μg/ml |
| β-Carotene | 0 | 11 μg/ml | 11 μg/ml |
| Lycopene | 0 | 5 μg/ml | 8 μg/ml |
| Vitamin D$_3$ | 0.2 μg/ml | 190 μg/ml | 640 μg/ml |
| Naphthalene | <0.5 μg/ml | 850 μg/ml | 1035 μg/ml |
| Anthracene | 0 | 69 μg/ml | 84 μg/ml |
| 2,3-Benzanthracene | 0 | 60 μg/ml | 59 μg/ml |

According to mass spectrometry results derivative 2 contained some unsubstituted digitonin; nevertheless, its presence could not be detected through its insolubility in water or chloroform. This behavior may be explained by a strong self-association of derivative 2; these self-associated species apparently have not only the capacity to complex and dissolve various lipophilic compounds, but also the contaminating digitonin.

Example VIII

Effects of digitonin and its derivatives on cells in culture.

Friend erythroleukemia cells, grown in Eagle's minimal essential medium with 10% calf serum were used.

Figure 3:
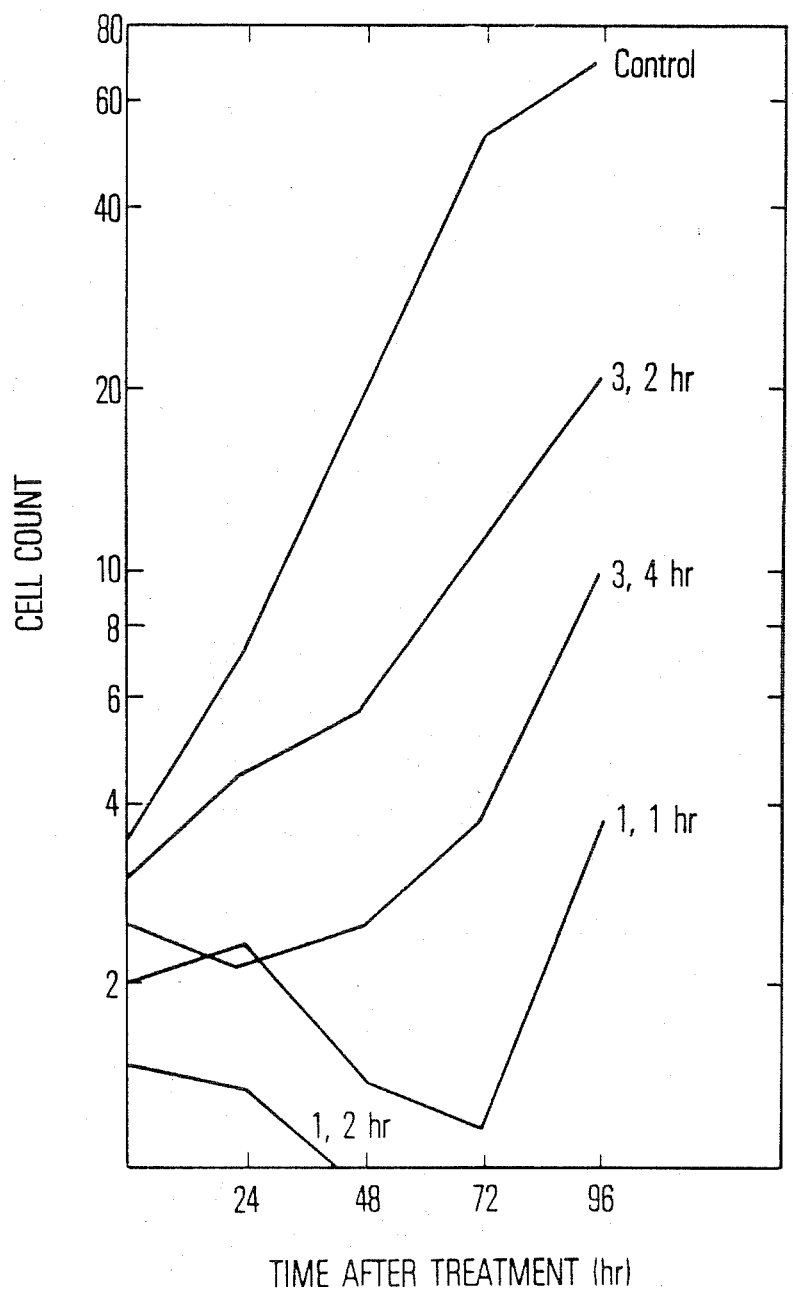
FIG. 3 graphically illustrates the effects of treatment by digitonin by a digitonin derivative according to the invention, and by serum free medium (control) on the growth of Friend Erythroleukemia cells in vitro. Cells were treated in serum free medium with compounds (0.1 mg/ml) for the times indicated. Thereafter cells were diluted into serum supplemented medium and their numbers followed daily. The cells were treated with the compounds indicated for the specified period of time, and then grown in normal cell medium for the time indicated on the x axis.

The toxicity of derivatives 2 and 3 to cells grown in culture was tested by effects of compounds on the growth curves of murine erythroleukemic cells for a five day growth period. A concentration of 0.1 mg/ml of derivative 3 added to the serum supplemented medium allowed growth and cell division, whereas addition of 0.01 mg/ml of digitonin led to cell destruction. The onset of cell damage was also considerably slower for derivative 3 than for digitonin itself. When cells were treated, in the absence of serum, with 0.1 mg/ml of digitonin, even 30 min. of treatment affected cell growth (which occurred later in serum supplemented medium), whereas with derivative 3 at least four hours of treatment were necessary to change the later growth (FIG. 3).

Example IX

Toxicity of digitonin derivatives.

Female mice C57Bl/6J, about nine weeks of age, were used for the experiments. The solution in phosphate buffered saline was infused by peristaltic pump (0.12 ml/hr) into the tail veins of the animals for about 20 hrs. Five animals were used per group and these were followed for three weeks after treatment.

The toxicity of derivative 3 to animals was tested using i.v. infusion of solutions of 3 into the tail veins of mice. Doses of 1000–2000 mg/kg of derivative 3 resulted in death, but doses of 500 mg/kg were without lethal effects.

When administered p.o. digitonin is toxic to mice but nontoxic to rats (>50 mg/kg), which tolerate even repeated applications (150 mg/kg/day). Digitonin is also nontoxic to monkeys in amounts up to 0.4% of food. On the other hand, in all parenteral applications digitonin is rather toxic; it produces acute inflammation when injected i.m. or s.c. (800 μg dose). This inflammation may be inhibited by anti-inflammatory drugs. Digitonin also exhibits strong hemolytic effects. For digitonin applied i.v. the LD$_{50}$ was found to be 4 mg/kg in rats. Since by i.v. infusion mice tolerated doses of 500 mg/kg of derivative 3 it is obvious that toxicity of digitonin was decreased by at least two orders of magnitude upon substitution by epoxides. Since pharmacokinetics of parenterally applied lipophilic drugs is very strongly affected by their relative water solubility, these derivatives 2 and 3 are useful in modifying the effects of lipophilic drugs.

Example X

Effects of derivative 3 on cell cultures contaminated with mycoplasmas

Mycoplasmas were eliminated from lymphoid cell lines and macrophage cell lines of murine origin by propagation of the cells in a conventional medium in the presence of from 50 to 100 μg/ml of derivative 3 isolated and freeze-dried as described in Example II. Over the course of the experiment (over three months), the cells grew normally and remained free of mycoplasma even with 2 to 3 passages per week. The cell lines tested are known to be especially sensitive to toxins.

What is claimed is:

1. A saponin-based polyether polyol having substitution of free hydroxyl groups in said polyol with an average of about 0.5 to 2 oxyalkylene groups per molecule of saponin and having the following properties:
   increased $LD_{50}$ compared to that of digitonin;
   decreased ability to precipitate cholesterol to at least a quarter of that of digitonin; and
   clear stability in water to a concentration of at least 10 g per liter; wherein said polyether polyol is selected from the group consisting of digitonin, digalonin, desglucodigitonin, gitonin, tigonin, digitonin-d' and mixture thereof.

2. The polyether polyol of claim 1 having the formula:

wherein $R_1$ and $R_2$ are H; $CH_2CHOHCH_3$ or $CH_2CHOHCH_2(OC_4H_8O)CH_2CHOHCH_2OH$ with the proviso that $R_1$ and $R_2$ are excluded from both simultaneously being H.

3. The polyether polyol of claim 1 wherein said substitution is with an average of about 1 to 1.4 oxyalkylene groups.

4. The polyether polyol of claim 1 being a reaction product of an alkoxylation reagent and a purified plant extract comprising saponins.

5. The polyether polyol of claim 4 wherein said extract is from a plant of genus Digitalis.

6. The polyether polyol of claim 5 wherein said plant is *Digitalis purpurea* and the extract comprises an extract of the seeds of said plant.

7. The polyether polyol of claim 6 wherein said saponin is digitonin.

8. The polyether polyol of claim 7 wherein said alkoxylation reagent is selected from the group consisting of alkylene oxide and diglycidyl ethers.

9. The polyether polyol of claim 8 wherein said alkylene oxide is propylene oxide.

10. The polyether polyol of claim 9 wherein said diglycidly ether is 1,4-butanediol diglycidyl ether.

11. The polyether polyol of claim 10 wherein said reaction product is a mixture of alkoxylated saponins.

12. The polyether polyol of claim 11 wherein said mixture comprises alkoxylated digitonin.

13. The polyether polyol of claim 1 being 2-hydroxyalkyl ethers of digitonin.

14. The polyether polyol of claim 1 being 2-hydroxyoxyalkyl ethers of digitonin.

15. The polyether polyol of claim 14 being hydroxyalkoxy-2-hydroxyalkyl ethers of digitonin.

16. A method for increasing the solubility of a lipophilic compound in aqueous solution comprising admixing a saponin-based polyether polyol according to claim 1 with the lipophilic compound in aqueous solution wherein said lipophilic compound is selected from the group consisting of β-ionene, retinol, β-carotene, lycopene, vitamin D, naphthalene, anthracene, 2,3-benzanthracene, and vitamin A.

17. A pharmaceutical composition for solubilizing a lipophilic pharmaceutical comprising a solubilizing amount of saponin-based polyether polyol according to claim 1, and a pharmaceutically-acceptable carrier, wherein said lipophilic pharmaceutical is selected from the group consisting of β-ionene, retinol, β-carotene, lycopene, vitamin D, naphthalene, anthracene, 2,3-benzanthracene, and vitamin A.

18. A pharaamaceutical composition for solubilizing a lipophilic pharmaceutical comprising a solubilizing amount of the compound according to claim 2, and a pharmaceutically-acceptable carrier, wherein said lipophilic compound is selcted from the group consisting of β-ionene, retinol, β-carotene, lycopene, vitamin D, naphthalene, anthracene, 2,3-benzanthracene, and vitamin A.

19. A method of administering a lipophilic pharmaceutical comprising admixing the pharmaceutical with a saponin-based polyether polyol according to claim 1, and parenterally or orally administering the admixture wherein said pharmaceutical is selected from the group consisting of β-ionene, retinol, β-carotene, lycopene, vitamin D, naphthalene, anthracene, 2,3-benzanthracene, and vitamin A.

20. The composition of claim 17, wherein the lipophilic pharmaceutical is selected from the group consisting of β-Ionene, Retinol, β-Carotene, Lycopene, Vitamin $D_3$, Naphthalene, Anthracene, 2,3-Benzanthracene, and Vitamin A.

21. A method for suppressing mycoplasmas in cell cultures comprising treating the cell culture with mycoplasma suppressing amount of a saponin-based polyether polyol according to claim 1.

* * * * *